(12) United States Patent
Bardat et al.

(10) Patent No.: US 7,727,743 B2
(45) Date of Patent: Jun. 1, 2010

(54) METHOD FOR STABILIZING A CRYOPRECIPITATE OF PLASMATIC PROTEINS FOR BEING SUBJECTED TO A VIRAL INACTIVATION THERMAL TREATMENT

(75) Inventors: Annie Bardat, Limours (FR); Edith Begin, Les Ulis (FR)

(73) Assignee: Laboratoire Francais du Fractionnement et des Biotechnologies, Les Ulis (FR)

( * ) Notice: Subject to any disclaimer, the term of this patent is extended or adjusted under 35 U.S.C. 154(b) by 808 days.

(21) Appl. No.: 10/563,620

(22) PCT Filed: Jul. 8, 2004

(86) PCT No.: PCT/FR2004/001788

§ 371 (c)(1),
(2), (4) Date: Jun. 19, 2006

(87) PCT Pub. No.: WO2005/004901

PCT Pub. Date: Jan. 20, 2005

(65) Prior Publication Data

US 2006/0247426 A1 Nov. 2, 2006

(30) Foreign Application Priority Data

Jul. 9, 2003 (FR) .................... 03 08403

(51) Int. Cl.
*C12P 21/04* (2006.01)
(52) U.S. Cl. .................. 435/69.6; 435/7.1; 530/350
(58) Field of Classification Search ........................ None
See application file for complete search history.

(56) References Cited

U.S. PATENT DOCUMENTS

| | | | |
|---|---|---|---|
| 4,470,968 A | 9/1984 | Mitra et al. | |
| 4,623,717 A | 11/1986 | Fernandes et al. | |
| 4,650,678 A | 3/1987 | Burk et al. | |
| 4,992,419 A | 2/1991 | Gruber et al. | |
| 5,399,670 A | 3/1995 | Bhattacharya et al. | |
| 5,831,027 A | 11/1998 | McIntosh et al. | |
| 5,919,443 A | 7/1999 | Michaelis et al. | |
| 6,623,717 B2 | 9/2003 | Angaiah et al. | |
| 2001/0049361 A1 | 12/2001 | Yamashita et al. | |

FOREIGN PATENT DOCUMENTS

CA 1260389 9/1989
EP 0094611 A2 11/1983
EP 0359593 A1 3/1990

OTHER PUBLICATIONS

Branovic et al. (Applied Biochemistry and Biotech. vol. 69, 1998, pp. 99-111).*
Winkelman L et al., "Severe Heat Treatment of Lyphilised Coagulation Factors", Current Studies in Hematology and Blood Transfusion, Karger, Basel, OH, No. 56, 1989, pp. 55-69.
Margolis J et al., "Stabilising Effect of Aminoacids on Factor VIII In Lyophilised Cryoprecipitate", Lancet The, Lancet Limited, London, GB, Dec. 8, 1984, p. 1345.
Kyte J et al., "A Simple Method for Displaying The Hydropatic Character of A Protein", Journal of Molecular Biology, London, GB, vol. 157, No. 1, May 5, 1982, pp. 105-132.
Jay A. Levy et al., "Inactivation by Wet and Dry Heat of AIDS-Associated Retroviruses During Factor VIII Purification from Plasma," The Lancet, Jun. 22, 1985, pp. 1456-1457.
Duncan P. Thomas, "Annotation: Reducing the risk of virus transmission by blood products," British Journal of Haematology, 1988, vol. 70, pp. 393-395.
S. J. Skidmore et al., "Serological Evidence That Dry Heating of Clotting Factor Concentrates Prevents Transmission of Non-A, Non-B Hepatitis," Journal of Medical Virology, 1990, vol. 30, pp. 50-52.
N. Heimburger et al., "Strategies to Produce Virus-Safe Blood Derivatives," Morgenthaler J-J (ed): Virus Inactivation in Plasma Products. Curr Stud Hematol Blood Transfus. Basel, Karger, 1989, vol. 56, pp. 23-33.
M. Wickerhauser et al., "Deveopment of Large-Scale Fractionation Methods: VI An Improved Method for Preparation of Antihemophilic Factor," Vox Sang., 1978, vol. 35, pp. 18-31.
P. Kistler et al., "Large Scale Production of Human Plasma Fractions: Eight Years Experience with the Alcohol Fractionation Procedure of Nitschmann, Kistler and Lergier," Vox Sang., 1962, vol. 7, pp. 414-424.

* cited by examiner

*Primary Examiner*—Hope A Robinson
(74) *Attorney, Agent, or Firm*—Birch, Stewart, Kolasch & Birch, LLP

(57) ABSTRACT

The invention relates to a method for obtaining cryoprecipitatable proteins, comprising a viral inactivation step by thermally treating a lyophilisate of these proteins, comprising, before rendering the proteins in the form of a lyophilisate, an initial addition step, to these proteins, of a stabilizing and solubilizing formulation containing a mixture consisting of arginine, at least one hydrophobic amino acid and of tribasic sodium citrate. The invention also relates to a concentrate consisting of at least one cryoprecipitable protein containing the stabilizing and solubilizing formulation introduced according to the method and being suited for therapeutic use.

18 Claims, No Drawings

METHOD FOR STABILIZING A CRYOPRECIPITATE OF PLASMATIC PROTEINS FOR BEING SUBJECTED TO A VIRAL INACTIVATION THERMAL TREATMENT

FIELD OF THE INVENTION

The present invention relates to a process for obtaining cryoprecipitable proteins from blood plasma, generally by cryoprecipitation or cold alcohol precipitation, using a freeze-drying step and a subsequent heat treatment of virus inactivation step of the freeze-dried product, comprising a step of addition of a stabilizing and solubilizing formulation allowing a freeze-drying of liquid compositions of said proteins and an easy resolubilization of the freeze-dried forms after the heat treatment of virus inactivation. In the scope of the invention, it is understood that the term "protein" covers the protein as such and the concentrates and fractions containing such a protein as well, especially for therapeutic use, single or in mixture with such other proteins. These concentrates and fractions are obtained by fractionation methods of human or animal plasma known in the prior art. Also the term "liquid composition of cryoprecipitable proteins" denotes a liquid composition including at least one protein characterized by its cold insolubility upon thawing frozen human or animal plasma, or by its insolubility upon cold precipitation by addition of an organic solvent, such as ethanol, to plasma.

BACKGROUND OF THE INVENTION

The use of therapeutic products obtained from human plasma, such as clotting factors, with the purpose of use in therapy, especially in the case of hereditary bleeding troubles, such as haemophilia, can be greatly jeopardized due the presence of viruses in blood products, which are a high risk to the haemophiliac patient. In spite of the rigorous selection of individual donors, there is a continuous risk of transmission of various viruses, especially of hepatitis and AIDS, and of yet unknown viruses, which may reveal themselves to be transmissible by blood products.

Therefore, the virus transmission should be avoided by means of suitable treatments of the different purified fractions obtained from donor plasma and intended to therapeutic use. On this account, various virus inactivation and elimination methods applied to various protein fractions obtained from blood plasma, are well known. For instance, solvent-detergent treatments, ultrafiltration and nanofiltration, pasteurisation or extended heating, can be mentioned. In the case of extended heat treatment, this can usually be applied only to plasma protein fractions subjected to a preliminary freeze-drying, while requiring heating temperatures of at least 70° C. in a laps of time between 50 and 100 hours, in order to obtain an optimal virus inactivation. However, under such severe heat treatment conditions, the sensitive and heat-instable plasma proteins undergo degradations, which yield important decrease of their biological functions.

In order to find a solution to this drawback, protecting excipients and stabilizers for plasma proteins are beforehand added to liquid compositions of proteins prior to freeze-drying, in order to fulfill a joint double aim. The first aim meets the need to stabilize, on one hand, the considered proteins during the freeze-drying and, on the other hand, the freeze-dried proteins during the storage, and the second aim corresponds to the need to protect the freeze-dried proteins during the heat treatment of virus inactivation.

A method of heating of protein fractions from freeze-dried plasma, Factor VIII or fibrinogen, disclosed in the patent EP 0 094 611, consists of heating the dry product at a temperature of 60° C. for from 72 to 96 hours. No specific composition of stabilizing excipients during the heat treatment is mentioned in this patent.

The canadian patent 1 260 389 mentions the incorporation of excipients, such as non-polar anions with molecular weights higher than 80, especially sugars, reducing sugars and amino acids, into liquid compositions of plasma proteins prior to freeze-drying, in order to stabilize these proteins against the dry heating for of about 72 hours at 68° C. However, the association of reducing sugars with amino acids leads to Maillard compounds, the properties of which do not account for the safety of the treated proteins (activity, immunogenicity, allergies, etc.). This treatment has to be carried out in vacuum or in an inert atmosphere.

Most of the stabilizing excipients may prove to be protective of plasma proteins fractions during the dry heat treatment thereof, at temperatures ranging from of 60° C. to 68° C. for of 30 to 96 hours (P. Thomas, British Journal of Haematology, 70, 1998, 393-395 and J. A. Levy et al., The Lancet, Jun. 22, 1985, 1456-1457). It was shown, however, that, in spite of a diminution of the viral titer after such a treatment under these conditions, infections, such as HIV, HBV, HBC and parvovirus B19 could, nevertheless, been transmitted (P. Thomas, supra). In view of their effective elimination, it was suggested to heat the freeze-dried plasma proteins fractions to higher temperatures. So S. J. Skidmore et al. (Journal of Medical Virology, 30, 1990, 50-52) have shown that a heat treatment of freeze-dried Factor VIII concentrates at a temperature of 80° C. for 72 hours avoids the transmission of HCV non-A and non-B virus. So the U.S. Pat. No. 5,831,027 discloses a process of heat treatment of a freeze-dried protein obtained from the cryoprecipitate of blood plasma, the fibrinogen, at a temperature of 80° C. for 72 hours, which allows to obtain a fibrinogen free of possible viruses, such as HBV, HBC or parvovirus B19. The stabilizing excipients, added to protect the fibrinogen composition during both the freeze-drying and the heat treatment of virus inactivation, include sucrose and/or an amino acid (arginine), Tris buffer and sodium citrate. L. Wilkelman et al. (Virus Inactivation in Plasma Products, Curr. Stud Hematol Blood Transfus., Basel, Karger, 1989, n° 56, 55-69) also show the need of addition of excipients to Factor VIII prior to freeze-drying and to heat treatment of virus inactivation at 80° C. for 72 hours. The described excipients are: NaCl, sodium citrate, Tris, $CaCl_2$ and sucrose.

Besides, as the different proteins obtained by plasma fractionation, having been subjected to freeze-drying and to heat treatment of virus inactivation, require a reconstitution in a suitable medium prior to their clinical use, this should be easy to carry out in a relatively short laps of time according to the requirements recommended by the European Pharmacopoeia. In this respect, studies of the heat stability of Factor VIII in a freeze-dried cryoprecipitate (J. Margolis et al., The Lancet, Dec. 8, 1984, 1345) containing, prior to freeze-drying, Synthamin 17% (Travenol Laboratories Ltd.), a mixture of natural amino acids suited to intravenous administration, have shown that a heat treatment at 80° C. for 16 hours leads not only to such an extent of degradation of Factor VIII that its activity equals to zero, but also to an impossibility of a redissolution of the cryoprecipitate after the mentioned steps. The U.S. Pat. No. 5,399,670 discloses a process facilitating the solubilization or the reconstitution of compositions of freeze-dried Factor VIII complex in purified water for injections, including a step of addition of arginine to a Factor VIII solution prior to freeze-drying thereof. This patent does not mention a heat treatment of virus inactivation. An addition of histidine and albumin can also be provided. The stabilizing excipients, mentioned in the previously cited U.S. Pat. No. 5,831,027, are also aimed to favour the dissolution of freeze-dried fibrinogen in pure water, prior to therapeutic use.

Nevertheless, the choice of a stabilizing formulation is governed by the specificity of the plasma proteins. Thus, in reference to a paper by N. Heimburger et al. (Virus Inactivation in Plasma Products., Curr Stud Hematol Blood Transfus., Basel, Karger, 1989, No. 56, 23-33), it is usually considered that a specific stabilizing formulation can be suited to only one protein fraction containing the given active proteins of interest. A further difficulty appears in the case where more complex protein fractions are considered, especially those, where all coagulation and haemostasis proteins obtained from plasma fractionation are taken into account. Moreover, carbohydrates, especially sucrose, may effectively be used as excipients for the stabilization and the redissolution of plasma proteins fractions, when the considered fractions are intended to be freeze-dried, then subjected to dry heat treatment, although their effect slows down the virus inactivation (N. Heimburger et al., supra). Therefore, the protein fractions treated in that way may not be completely virus-free and their use in clinics is thus restricted. Furthermore, some carbohydrates, such as maltose or sucrose, cannot be safely used with subjects suffering from kidney deficiency and/or diabetes.

SUMMARY OF THE INVENTION

Therefore, considering the medical needs of some proteins responsible for clotting and heamostasis, especially cryoprecipitable proteins, the Applicant attempted to develop a simple, carbohydrate-free and Tris buffer-free composition, compatible with therapeutic use, which, added to the liquid composition of cryprecipitable proteins, confers a good protection to all considered active proteins of interest during and after the freeze-drying thereof, on one hand, and, on the other hand, against the heat shocks necessary to the virus destruction and which, in the time, enables a reduced time of the resolubilization of the freeze-dried forms of these proteins.

To this end, considering that the addition of arginine to liquid compositions of cryoprecipitate proteins provides a protective effect during and after the freeze-drying, while allowing the solubilization of their freeze-dried forms, but not ensuring their stability against the heat treatment of virus inactivation, the Applicant investigated different compounds, single or in mixture, the addition of which to arginine should provide a protection against heat denaturation. Thus, the Applicant has surprisingly found that the addition to arginine, a very hydrophilic amino acid, of at least one hydrophobic amino acid, preferably selected from the most hydrophobic acids according to Kyte et al. (J. Mol. Biol., 157, 105-132, 1982), and of trisodium citrate, enabled the stabilization of the cryoprecipitable proteins during and after freeze-drying, with a marked improvement of the solubilization of the freeze-dried forms after the heat treatment of virus inactivation.

Consequently, the invention relates to a process for obtaining cryoprecipitable proteins including a virus inactivation step by heat treatment of a freeze-dried form of said proteins, characterized in that it includes, before transforming the proteins into a freeze-dried form, an initial step of addition to said proteins of a stabilizing and solubilizing formulation comprising a mixture of arginine, at least one hydrophobic amino acid and trisodium citrate.

DETAILED DESCRIPTION OF THE PREFERRED EMBODIMENTS

Thus, the addition of the stabilizing and solubilizing formulation in the process of the invention enables to maintain a satisfactory level of biological activity of the cryoprecipitable proteins obtained from blood plasma after freeze-drying and heat treatment of virus inactivation, even if the last one is severe, and to allow a reduced time of resolubilization, while preserving the character of limpidity of the reconstituted solution of the freeze-dried form. Moreover, this formulation has the advantage of simplicity, of universality and of easy implementation on industrial scale, with appreciable savings of time.

Preferably, the stabilizing and solubilizing formulation used in the process of invention is constituted of the sole mixture of arginine, at least one hydrophobic amino acid and trisodium citrate. Such a formulation, constituted exclusively of these three compounds, presents especially the advantage to associate reduced time and costs of preparation on industrial scale, thanks to the presence of a minimal, but efficient number of additives.

Any hydrophobic amino acid (according to Kyte et al. supra), such as valine and phenylalanine, is suitable in the frame of the invention but the advantageous choice is leucine, isoleucine or a mixture thereof.

The stabilizing and solubilizing formulation also contains trisodium citrate allowing, on one hand, to adjust the pH of the liquid compositions of cryoprecipitable proteins prior to the above-mentioned treatments and, on the other hand, to increase the protective effect thereof, provided the concentration be adjusted.

Finally, glycine and/or lysine can furthermore be added to the stabilizing and solubilizing formulation.

Also, if needed, stabilizing additives known in the art, can be added.

In the context of the invention, the stabilizing and solubilizing formulation, comprising the mixture of the three components of interest can be added to a liquid composition of cryoprecipitable proteins, or the cryoprecipitable proteins can be dissolved in an aqueous solution of the formulation comprising the mixture of the three components of interest.

The concentrations of the different additives considered for the stabilizing formulation are selected by those skilled in the art with the aim to obtain the expected stabilizing effect. Advantageously, the concentrations of each additive per liter of liquid compositions of cryoprecipitable proteins are the following:

- arginine, from 25 to 50 g/l and preferably from 35 to 45 g/l (referring to the U.S. Pat. No. 5,399,670);
- trisodium citrate, from 0.5 to about 12 g/l;
- leucine, isoleucine and mixtures thereof, from 5 to 15 g/l, and preferably from 9 to 11 g/l; and
- glycine and/or lysine, each from 5 to 5 g/l, and preferably from 1.5 to 2.5 g/l.

In the frame of the invention, the freeze-drying of beforehand frozen liquid compositions of proteins is carried out according to conventional methods with use of current equipment, according to implementation conditions known by those skilled in the art. Advantageously, the freeze-drying is carried out at temperatures between −40° C. and −30° C. for about 48 hours.

The heat treatment of virus inactivation is carried out in a way as to effectively inactivate the virus. It is carried out preferably at temperatures between 80° C. and 90° C. for 72 hours.

Although the heat treatment of virus inactivation allows to obtain a virus-free freeze-dried product, the process may comprise, prior to the step of addition of the stabilizing and solubilizing formulation to a liquid composition of cryoprecipitable proteins, at least one additional virus inactivation and/or elimination step of the said liquid compositions by solvent-detergent and/or nanofiltration, for instance on filters of 35 nm, in order to finally ensure a total and complete inactivation and elimination of viruses.

Thus, the implementation of the process leads to freeze-dried and virus-inactivated cryoprecipitable proteins which, once reconstituted in a liquid pharmaceutically compatible medium, such as pure water for injections, can be directly injected to a patient. This therapeutic quality of cryoprecipitable proteins is obtained thanks to the stabilizing and solubilizing formulation, which enables the use of all the above-mentioned treatments, especially the virus inactivation and elimination treatments, whereas the biological activity of these treated cryoprecipitable proteins and the dissolution characteristics of the freeze-dried form are maintained.

The stabilizing and solubilizing formulation, used according to the process of the invention, applies to cryoprecipitable proteins, such as Factor VIII, von Willebrand Factor, Factor XIII, fibrinogen and fibronectin, obtained by methods of fractionation of blood plasma known to those skilled in the art. The stabilizing and solubilizing formulation also applies to different concentrates of semi-purified proteins, obtained for example by extraction/solubilization in Tris buffer and adsorption on alumina gel, as described by Wickerhauser et al., (Vox Sang., 35, 18-31, 1978). A thus obtained concentrate, enriched by Factor VIII and von Willebrand Factor, can be heated under the conditions disclosed in the Patent EP 0 094 611.

This formulation is also suitable for the stabilization and solubilization of the purified proteins or fractions enriched by each of the clotting factors, such as those obtained especially after the implementation of chromatographic methods disclosed, for example, in the patent EP 0 359 593, being afterwards freeze-dried and subjected to a heat treatment of virus inactivation. Moreover, this formulation is suitable for the stabilization of purified fibrinogen obtained from the cryoprecipitate of plasma or from plasma by cold alcohol precipitation, such as described by Kistler et al. (Vox Sang., 7, 1962, 414-424). It should be noted that in the context of the invention, during the purification of fibrinogen from a cryoprecipitate by any fractionation technique known to those skilled in the art, it is always accompanied by a low content of Factor XIII (FXIII), not damageable to its therapeutic activity.

This process is particularly advantageous because it can be applied to all cryoprecipitable proteins, or at least to one protein selected from thereof and, especially, from Factor VIII, von Willebrand Factor, Factor XIII, fibrinogen and fibronectin.

The invention also relates to concentrates of at least one cryoprecipitable protein, especially for therapeutic use, comprising the stabilizing and solubilizing formulation according to the process of the invention.

Finally, the invention relates to a stabilizing and solubilizing formulation for the cryoprecipitable proteins intended to be subjected to freeze-drying and a heat treatment of virus inactivation, comprising a mixture of arginine, at least one hydrophobic amino acid and trisodium citrate. Preferably, the stabilizing and solubilizing formulation is constituted of the said mixture of arginine, at least one hydrophobic amino acid and trisodium citrate.

The following examples describe the invention without limiting its scope.

Example 1

A cryoprecipitate, consisting for the most part of Factor VIII, von Willebrand Factor, Factor XIII, fibrinogen and fibronectin, was resolubilized in a stabilizing and solubilizing formulation of the invention comprising the mixture of compounds given in Table 1 (Solution A). The concentration of proteins is of about 15 g/l.

TABLE 1

| COMPOUNDS AND CONCENTRATIONS THEREOF (SOLUTION A) | |
|---|---|
| Compounds | Concentration (g/l) |
| Arginine | 40 |
| Iso-leucine | 10 |
| Trisodium citrate | 2.5 |
| Lysine | 2 |
| Glycine | 2 |

After homogenisation of the mixture, the thus obtained solution is filtered through filters of 0.45 μm, and 5 ml are taken and put into a vial. Afterwards, the solution is subjected to a freeze-drying at −30° C. for 48 hours. It is proceeded in the same way with a reference solution comprising the same cryoprecipitate as the former one, but which was resolubilized in a standard formulation comprising a mixture of Tris (2.4 g/l), trisodium citrate (5.88 g/l) and NaCl (1.16 g/l), respectively (Solution B).

Following to the freeze-drying, both obtained freeze-dried cryoprecipitates, namely one comprising the formulation of the invention and the other the standard formulation, are resolubilized in 5 ml of pure water for injections (referred to Solution A' and Solution B', respectively). Experiments were then carried out in order to assess the ability of standard formulations and of those of the invention to protect or to stabilize the considered proteins as a whole during the freeze-drying, together with the solubilization of the obtained freeze-dried forms. For that purpose, the following three parameters are assessed for each Solution A' and B': appearance of the freeze-dried form before redissolution, the time of redissolution of the freeze-dried form in purified water for injections and the turbidity of the thus obtained solution, together with the activities and the amounts of different proteins, by means of methods known to those skilled in the art. The different measurement results are shown in Table 2, where the units of volume are related to the solution of the freeze-dried product reconstituted with 5 ml of purified water for injections.

TABLE 2

| | Solution A' | Solution B' |
|---|---|---|
| Appearance of the dry freeze-dried form | yellowish | yellowish, freeze-dried product retracted |
| Time of redissolution (min) | 6.58 | 10.72 |
| Turbidity (NTU*) | 18.1 | 29 |
| Clottable fibrinogen (g/l) | 12.6 | 14.5 |
| Weight of fibrinogen (g/l) | 11.6 | 11.2 |

TABLE 2-continued

|  | Solution A' | Solution B' |
|---|---|---|
| Factor VIII activity (IU/ml) | 6.7 | 6.3 |
| von Willebrand Factor activity (FvW: RCo; IU/ml) | 8.1 | 8.1 |
| Factor XIII activity (IU/ml) | 1.51 | 1.24 |
| Fibronectin (mg/ml) | 5.85 | 5.52 |

*NTU: Normalized Turbidity Units

The obtained results show in the first place that the addition of a formulation of the invention (Solution A) to proteins of the cryoprecipitate, in comparison to the standard formulation (Solution B), allows to markedly reduce, of about 40%, the time of redissolution of the freeze-dried form. It is also noted that the formulation A yields better results of turbidity, which suggest a reduced presence of water insoluble degradation products in comparison to the solution B. In both cases, Solutions A and B restore in the whole the same quantities and activities of the considered proteins after freeze-drying.

Example 2

Both above-mentioned freeze-dried proteins from the cryoprecipitate, namely one comprising the formulation of the invention and the other one the standard formulation, are dry heated for 72 hours at 80° C. The heated freeze-dried proteins of the cryoprecipitate including a formulation of the invention (Solution A) are reconstituted in 5 ml of pure water for injections (Solution A"). It is noted that the heated freeze-dried proteins of the cryoprecipitate comprising the standard formulation (Solution B) cannot be resolubilized. This impossibility of redissolution can be explained by the presence of heat-denatured and insoluble proteins, which is an indication that the solution B does not stabilize these proteins during the heat treatment. As in the Example 1, however, the same experiments are carried out in order to evaluate the capability of the formulation of the invention to stabilize and to solubilize the whole of the considered proteins together after the heat treatment of virus inactivation carried out with their freeze-dried forms of Example 1. The different results of measurements are shown in Table 3 where the units of volume are related to the solution of the freeze-dried product reconstituted with 5 ml of purified injection water.

TABLE 3

|  | Solution A" |
|---|---|
| Appearance of the dry freeze-dried form | lemon yellow |
| Time of redissolution (min) | 3.73 |
| Turbidity (NTU*) | 18.3 |
| Clottable fibrinogen (g/l) | 13.3 |
| Weight of fibrinogen (g/l) | 11.7 |
| Factor VIII activity (IU/ml) | 5.6 |
| von Willebrand Factor activity (FvW: RCo; IU/ml) | 6.0 |
| Factor XIII activity (IU/ml) | 1.86 |
| Fibronectin (mg/ml) | 5.93 |

*NTU: Normalized Turbidity Unit

The comparison of the results of measurements obtained for the Solutions A' and A", extracted from Tables 1 and 2 respectively, surprisingly show that the Solution A, formulation of the invention, allows to obtain a very high reduction, of about 50%, of the time necessary to the redissolution of the heat-treated proteins compared to that obtained after freeze-drying, without noticeable losses of their biological functions.

Example 3

A batch of fibrinogen, isolated and purified from a cryoprecipitate by the Kistler et al. method was solubilized at a ratio of 15 g/l in a control formulation constituted of a mixture of trisodium citrate (2.5 g/l), lysine (2 g/l) and glycine (2 g/l) (Solution C). A concentrated solution of fibrinogen is thus obtained. Different amino acids are added to this solution in order to study their influence on the time of redissolution of the freeze-dried fibrinogen before and after heating. The obtained solutions and concentrations of amino acids are shown in the Table 4.

TABLE 4

| Solution | Amino acid (g/l) |
|---|---|
| C |  |
| C1 | C + valine (5 g/l) |
| C2 | C + leucine (5 g/l) |
| C3 | C + arginine (10 g/l) |
| C4 | C + isoleucine (10 g/l) |
| C5 | C + isoleucine (10 g/l) + arginine (10 g/) |

Afterwards, the different solutions (Solutions C to C5) are filtered and 10 ml of each solution are subjected to a freeze-drying and a heat treatment according to Example 1. The respective freeze-dried products are taken up in 10 ml of pure water for injections and the time necessary to a complete redissolution of the freeze-dried products is measured. The results are shown in Table 5.

TABLE 5

| Solution | Time of redissolution before heating (min) | Time of redissolution after heating (min) |
|---|---|---|
| C | 32.66 | 61.50 |
| C1 | 15.22 | 8.05 |
| C2 | 16.3 | 22.93 |
| C3 | 6.0 | 12.69 |
| C4 | 11.25 | 10.75 |
| C5 | 5.7 | 4.85 |

The results show that the Solution C5 of the invention yields the shortest time of redissolution.

In order to also show the capability of the considered fibrinogen solutions to be stabilized during the freeze-drying and the heating of the dry forms, depending on the nature of the added amino acid, turbidity measurements of the former reconstituted solutions were carried out. The Table 6 shows the measurements of turbidity before heating and after heating of the freeze-dried Solutions C to C5.

TABLE 6

| Solution | Turbidity before heating (*NTU) | Turbidity after heating (*NTU) | Increase (%) |
|---|---|---|---|
| C | 24.25 | 34.65 | 42.9 |
| C1 | 18.04 | 22.83 | 26.6 |
| C2 | 18.48 | 24.68 | 35.6 |
| C3 | 15.44 | 18.80 | 21.8 |
| C4 | 13.02 | 16.06 | 23.3 |
| C5 | 10.98 | 11.88 | 8.2 |

(*NTU): Normalized Turbidity Units

The results show without any doubt that a formulation of the invention (Solution C5) yields the least difference in the turbidity of the reconstituted solutions, before and after heating, that was rendered in an increase of only 8.2%, compared with the Solution C the increase of which is of 42.9%.

Example 4

Solutions C, C3 a C5 from Example 3, containing an other batch of fibrinogen, are freeze-dried and heated at 80° C. for 72 hours. Afterwards, the corresponding freeze-dried forms are taken up in 10 ml of pure water for injections and the following parameters are measured:

time of redissolution, amount of insoluble multimers, turbidity and filterability of the reconstituted solutions by methods known to those skilled in the art. Especially the filterability allows to evaluate the degree of denaturation of a protein, fibrinogen in the present case, however, does not allow to define the factor(s) of denaturation which can be proportionate to the amount of particles, fibrils or multimers. Just the same, the multimer content is also proportionate to the degree of denaturation of fibrinogen and is measured by electrophoresis (SDS Page). The filterability assay consists of measurement of the recovered filtered volume of a solution through a filter with a sufficient porosity in order to ensure the sterilisation of the solution, that is to say of $0.20\pm0.02$ μm and of 25 mm of diameter by use of a syringe containing 10 ml of the solution to be examined. The recovered filtered volume expresses the importance of the clogging of the filter by the degradation products. Thus, higher the recovered volume, lower is the degradation of fibrinogen. The results of different measurements are shown in Table 7.

TABLE 7

| Solution | Filterability (ml) | Redissolution time (min) | Amount of multimers (%) | Turbidity (*NTU) |
|---|---|---|---|---|
| C | 7 | 20 | 10 | 26 |
| C3 | 10 | 20 | 10 | 21 |
| C4 | 10 | 10 | 5 | 11 |
| C5 | 10 | 4 | <3 | 11 |

(*NTU): Normalized Turbidity Units

The four here-above analysed parameters suggest that a formulation of the present invention (Solution C5) is particularly suitable for the stabilization and the redissolution of the freeze-dried form of heated fibrinogen. The reconstituted freeze-dried fibrinogen has a filterability related to the surface of the filter of about 2 ml/cm².

In order to demonstrate the stabilizing and solubilizing powers of the Solution C5 according to the invention with regard to fibrinogen, even under the severe conditions of the heat treatment, the Solutions C3 and C5 containing a different batch of fibrinogen, were freeze-dried and heated at 90° C. for 72 hours. Besides the investigation of the above four parameters, additional assays consisting of the measurement of the amount of degradation products of fibrinogen (DPF) were carried out. In the frame of this example, the DPF (μ/ml) are peptides of different size generated upon the denaturation of fibrinogen. The higher this value, the higher appears its degradation, and is liable to form, for example clots. The results of different measurements are shown in Table 8.

TABLE 8

| Solution | Filterability (ml) | Time of redissolution (min) | Amount of multimers (%) | Turbidity (*NTU) | DPF (μg/ml) |
|---|---|---|---|---|---|
| C3 | ≦6 | 10 | 10 | 16 | 750 to 1250 |
| C5 | 10 | 10 | 10 | 11 | 625 to 750 |

The above results demonstrate that, in spite of the very severe heating conditions, the formulation of the invention (Solution C5) still provides a protection and allows a solubilization of the fibrinogen after freeze-drying and heat treatment at 90° C. for 72 hours, which is depicted in the good values of the investigated parameters. The freeze-dried form of the reconstituted fibrinogen has also a filterability related to the surface of the filter of about 2 ml/cm².

Example 5

This example relates to the influence of the concentration of trisodium citrate contained in a formulation of the invention (Solution A) on the stabilization and the solubilization of a fibrinogen solution intended to be freeze-dried and heated at 80° C. for 72 hours. A batch of fibrinogen, obtained from a cryoprecipitate, was solubilized at a ratio of 15 g/l and homogenized in the Solution A wherein the concentration of trisodium citrate varied from one solution to another. Four solutions were obtained, referred to Solutions A1, A2, A3 and A4, respectively, containing 0.5 g/l, 1 g/l, 2 g/l and 11.2 g/l, respectively, of trisodium citrate. Afterwards, these solutions were filtered as described in Example 1, and 5 ml of each solution were taken and put into a vial. The above four solutions containing the fibrinogen were subjected to a freeze-drying and a heat treatment mentioned in Example 1. Afterwards, the four not-heated freeze-dried fibrinogens, on one hand, and heated, on the other hand, were resolubilized in 5 ml of pure water for injections in order to yield the above four solutions A1, A2, A3 and A4. Experiments were carried out in order to evaluate the influence of the concentration of trisodium citrate in the formulation of the invention on the capability to protect the fibrinogen during freeze-drying and to solubilize it after heating of the freeze-dried forms, compared to solutions which were not subjected to any of the preceding treatments (corresponding control solutions). For that purpose, the following parameters are measured for each Solution A1, A2, A3 and A4: time of redissolution of the freeze-dried form in pure water for injections, turbidity of the thus obtained solution, amounts of insoluble multimers, of weight of fibrinogen and of clottable fibrinogen, by methods known to those skilled in the art. The different results of measurements are shown in the Table 9 where the units of volume are related to the solution of the freeze-dried product reconstituted with 5 ml of purified water for injections.

TABLE 9

|  | Prior to freeze-drying | | | | After freeze-drying | | | | After heating (80° for 72 h) | | | |
| --- | --- | --- | --- | --- | --- | --- | --- | --- | --- | --- | --- | --- |
|  | A1 | A2 | A3 | A4 | A1 | A2 | A3 | A4 | A1 | A2 | A3 | A4 |
| Amount of multimers (%) | 8.3 | 6.6 | 7.3 | 7.5 | 6.9 | 5.6 | 5.8 | 4.2 | 6.3 | 6.2 | 5.9 | 5.2 |
| Turbidity *NTU | 11.0 | 11.0 | 10.9 | 10.1 | 11.3 | 11.1 | 10.9 | 10.1 | 11.6 | 11.3 | 11.2 | 10.3 |
| Clottable fibrinogen (g/l) | 17.3 | 17.2 | 17.3 | 16.3 | 14.9 | 14.3 | 14.6 | 14.2 | 14.9 | 14.9 | 15.2 | 15.2 |
| Weight of fibrinogen (g/l) | 16.6 | 16.1 | 16.0 | 15.8 | 16.2 | 16.1 | 16.0 | 15.2 | 16.7 | 15.7 | 16.9 | 16.1 |
| Time of redissolution (min) | — | — | — | — | 5.50 | 10.87 | 6.37 | 10.03 | 10.35 | 9.83 | 11.55 | 9.95 |

*NTU = Normalized Turbidity Units

The obtained results show that a concentration selected in the range of values of 0.5 to about 12 g/l of trisodium citrate in one of the above formulations of the invention not only enables a satisfactory stabilization of the fibrinogen during freeze-drying and heat treatment, in comparison to the control solutions, but also to maintain the whole identical times of redissolution of the freeze-dried fibrinogen compared to the dry heated fibrinogen.

Example 6

This example relates to the influence of the concentration of trisodium citrate contained in a formulation according to the invention (Solution A) on the stabilization of Factor XIII contained in a fibrinogen solution to be freeze-dried, on one hand, and, on the other hand, heated at 80° C. for 72 hours. These two proteins, which were obtained from a cryoprecipitate, were resolubilized at a ratio of 15 g/l (fibrinogen+Factor XIII) and homogenized in two formulations according to the invention (Example 1) containing 2.5 g/l (Solution A) and 11.2 g/l (Solution A4) of trisodium citrate, respectively. Prior to the freeze-drying, the Solutions A and A4 have been subjected to the treatments described in Example 1. Both freeze-dried forms of fibrinogen and of Factor XIII not heated, on one hand, and heated, on the other hand, are afterwards resolubilized in 5 ml of purified water for injections in order to yield both above solutions A and A4. The activity of FXIII expressed in IU/ml (of purified water for injections) and the FXIII-antigen in IU/ml were measured, as well as the rate of activity of FXIII:FXIII-antigen (referred to R) by classical analytical methods. The different results of measurements are shown in Table 10.

TABLE 10

|  | Freeze-dried product not heated | | | Freeze-dried product heated | | |
| --- | --- | --- | --- | --- | --- | --- |
|  | FXIII activity (IU/ml) | FXIII-antigen (IU/ml) | R | FXIII activity (IU/ml) | FXIII-antigen (IU/ml) | R |
| Sol. A | 1.5 | 2.25 | 0.60 | 1.3 | 2.8 | 0.46 |
| Sol. A4 | 9.9 | 8.22 | 1.2 | 8.6 | 8.15 | 1.06 |

The results show a slight diminution of the rate R for each freeze-dried form when heat-treated, compared to not heated freeze-dried forms. Furthermore, it is noted that the diminution of the rate R is less important when the citrate content is higher. Moreover, this Table reveals that when the concentration of citrate of one solution increases compared to an other, in this case Solutions A and A4, and when these are freeze-dried, the rate R also increases. The same phenomena is noted when the freeze-dried forms are heated. Consequently, the concentration of citrate influences the stabilization of FXIII, which is also demonstrated by the values of the different activities.

Example 7

In this example, the four solutions prepared according to Example 5 are reconstituted after freeze-drying and heat treatment (80° C. for 72 hours). The following Table 11 shows the measurements of FXIII activity expressed in IU/ml (of purified water for injections) and of FXIII-antigen in IU/ml, as well as the rate of activity FXIII:FXIII-antigen (referred to R) depending on variations of citrate concentrations in the solutions.

TABLE 11

| Solution | FXIII activity (IU/ml) | FXIII-antigen (IU/ml) | R |
| --- | --- | --- | --- |
| A1 | 4.8 | 6.35 | 0.76 |
| A2 | 4.7 | 6.38 | 0.74 |
| A3 | 5.5 | 6.49 | 0.85 |
| A4 | 6.0 | 5.7 | 1.05 |

The obtained results show that higher the concentration of trisodium citrate in the formulation of the invention, lower is the degradation of FXIII.

The invention claimed is:

1. A process for obtaining a cryoprecipitable protein comprising:
   (a) contacting a composition containing a cryprecipitable protein of interest with a stabilizing and solubilizing formulation comprising a mixture of arginine, at least one hydrophobic amino acid and trisodium citrate;
   (b) transforming said protein composition into a freeze-dried protein; and
   (c) performing a virus inactivation step by heat treatment of said freeze-dried protein.

2. The process of claim 1, wherein the formulation consists essentially of the mixture of arginine, the hydrophobic amino acid and the trisodium citrate.

3. The process of claim 1, wherein arginine is present in a concentration from 25 to 50 g/l.

4. The process of claim 3, wherein the concentration of arginine is from 35 to 45 g/l.

5. The process of claim 1, wherein the trisodium citrate is present in a concentration from 0.5 to about 12 g/l.

6. The process of claim 1, wherein the hydrophobic amino acid is leucine, iso-leucine or a mixture thereof.

7. The process of claim 6, wherein leucine, iso-leucine or mixture thereof are present in a concentration from 5 to 15 g/l.

8. The process of claim 6, wherein the concentration of leucine or iso-leucine or mixture thereof is from 9 to 11 g/l.

9. The process of claim 1, wherein the formulation of step (a) further contains glycine and/or lysine.

10. The process of claim 9, wherein glycine and lysine are each present in a concentration from 1 to 5 g/l.

11. The process of claim 9, wherein each concentration of glycine and lysine is from 1.5 to 2.5 g/l.

12. The process of claim 1, wherein the step (b) is carried out at temperatures between −40° C. and −30° C. for 48 hours.

13. The process of claim 1, wherein step (c) is carried out at temperatures between 80° C. and 90° C. for 72 hours.

14. The process of claim 1, further comprising, prior to step (a), at least one step of virus inactivation and/or elimination from the said composition of cryoprecipitable protein by solvent-detergent and/or by nanofiltration on filters of 35 nm.

15. The process of claim 1, wherein said process uses at least one of the proteins selected from the group consisting of Factor VIII, von Willebrand Factor, Factor XIII, fibrinogen and fibronectin.

16. A concentrate comprising a cryoprecipitable protein comprising a stabilizing and solubilizing formulation added to the protein prepared by the process of claim 1.

17. The of claim 16 intended for wherein said concentrate is used as a therapeutic.

18. The concentrate of claim 16, comprising a filterability of about 2 ml/cm$^2$ on a filter with a porosity of 0.20±0.02 μm.

* * * * *